(12) United States Patent
Riley et al.

(10) Patent No.: US 7,836,747 B2
(45) Date of Patent: Nov. 23, 2010

(54) STANDARD MOISTURE CORRECTION FOR FIBER TESTING

(75) Inventors: C. Roger Riley, Knoxville, TN (US); Anja C. Schleth, Knoxville, TN (US); Hossein M. Ghorashi, Knoxville, TN (US); Michael E. Galyon, Knoxville, TN (US)

(73) Assignee: Uster Technologies AG, Uster (CH)

( * ) Notice: Subject to any disclaimer, the term of this patent is extended or adjusted under 35 U.S.C. 154(b) by 365 days.

(21) Appl. No.: 12/067,364

(22) PCT Filed: Oct. 12, 2006

(86) PCT No.: PCT/CH2006/000569
§ 371 (c)(1),
(2), (4) Date: Mar. 19, 2008

(87) PCT Pub. No.: WO2007/041889
PCT Pub. Date: Apr. 19, 2007

(65) Prior Publication Data
US 2008/0257010 A1     Oct. 23, 2008

Related U.S. Application Data

(60) Provisional application No. 60/727,013, filed on Oct. 14, 2005.

(51) Int. Cl.
*G01D 18/00*     (2006.01)
*G01N 33/00*     (2006.01)
(52) U.S. Cl. .......................... 73/1.01; 73/866
(58) Field of Classification Search ................... 73/866, 73/1.01
See application file for complete search history.

(56) References Cited

U.S. PATENT DOCUMENTS

| 4,180,617 | A | * | 12/1979 | Reinehr et al. | ............. 428/398 |
| 4,986,108 | A | | 1/1991 | Wilder | |
| 5,289,381 | A | * | 2/1994 | Demuth et al. | ............. 700/142 |
| 5,361,450 | A | | 11/1994 | Shofner | |
| 5,892,142 | A | | 4/1999 | Ghorashi et al. | |

FOREIGN PATENT DOCUMENTS

EP     0373058     6/1990

\* cited by examiner

*Primary Examiner*—Hezron Williams
*Assistant Examiner*—Nathaniel Kolb
(74) *Attorney, Agent, or Firm*—Luedeka, Neely & Graham, P.C.

(57) ABSTRACT

A method for standardizing a reading taken on a fiber sample, including the steps of measuring a moisture content of the fiber sample, taking the reading on the fiber sample, and correcting the reading to a standardized reading that adjusts for a difference between the reading at the measured moisture content of the fiber sample and a standardized reading at about 7.5% moisture content.

5 Claims, 4 Drawing Sheets

STANDARD MOISTURE CORRECTION FOR FIBER TESTING

This application claims priority on U.S. provisional application Ser. No. 60/727,013 filed 2005 Oct. 14.

This invention relates to the field of fiber processing and testing. More particularly, this invention relates to correcting to standardized laboratory conditions the measurements that are taken on fibers at nonstandard laboratory conditions.

FIELD

Background

Fiber testing, such as for length and strength, is typically performed in a temperature and humidity controlled environment. Internationally used standards such as the American Society for Testing and Materials (ASTM) Standard Number D-1776 prescribe standard laboratory conditions for testing textile materials such as fibers at 21° Celsius +/−1° and 65% relative humidity +/−2%.

One reason for controlling the temperature and humidity of the fibers during testing in this manner is that the moisture content of such fibers tends to affect characteristics of the fibers, such as length and strength. For example, fibers with higher moisture content tend to exhibit less crimping, and thus fiber length tests tend to report these fibers as having a greater length. Further, possibly due to increased hydrogen bonding between adjacent water molecules in the space between cellulose sheaths and other effects, strength tests on fibers with higher moisture content tend to report such fibers as having a greater strength.

Thus, all fiber testing is most preferably performed at any standard laboratory conditions. In this manner, tests that are performed in different geographical locations and at different times, and which might otherwise have different temperature and humidity conditions in the laboratory, can be reliably compared one to another. When tested under the standardized ASTM conditions given above, it has been assumed that all cotton fibers will equilibrate to a given moisture content of 8.0%. (Re-arranged Order)

However, most fiber testing is not performed under any standardized laboratory conditions. In such nonstandard laboratory conditions, the moisture in the cotton fiber is in equilibrium with the moisture in the air. As a result, the measurements not only may be at different levels in different laboratories but also vary throughout the day as the conditions in an individual laboratory change.

Previous attempts at moisture corrections to the length and strength data have focused on the use of either external moisture measurements or measurements of temperature and relative humidity. The correction is then performed using a correlation between either the directly measured or estimated moisture content and measurements made at standard laboratory conditions. In this manner, measurements taken in nonstandard laboratory conditions can be compared to measurements taken in standard ASTM laboratory conditions at an assumed moisture content of 8.0%.

Unfortunately, there does not appear to be a good correlation between such corrected nonstandard laboratory condition measurements and any standard laboratory condition measurements. What is needed, therefore, is a method that provides a better correlation between the results obtained for fibers tested at standard laboratory conditions, and the corrected results obtained for fibers tested at nonstandard laboratory conditions.

SUMMARY

The above and other needs are met by a method for standardizing a measurement of a fiber sample, including the steps of measuring a moisture content of the fiber sample actually being measured during the time of measurement, measuring the fiber sample, and correcting the measurement to a standardized moisture measurement that adjusts for a difference between the measurement at the measured moisture content of the fiber sample and a standardized moisture measurement. An appropriate standardized moisture content is about 7.5% moisture content for ASTM laboratory conditions. If one's selected standard laboratory conditions are different than ASTM conditions, then one can select a different standardized moisture content. Preferably, the measurement includes at least one of fiber length and fiber strength.

Different cotton samples equilibrate to different moisture contents, depending at least in part upon a number of different factors, as described in more detail hereafter. Measurements at different combinations of temperature and relative humidity on a sample set of approximately forty cottons were used to develop the algorithm which corrects for the difference is moisture content between the measured moisture content and the standardized moisture content. These cottons were chosen to span the range of fiber properties from growth areas throughout the world. It has been determined that the analysis to determine the correction must include the actual equilibrium moisture at standard conditions for each sample in this sample set used to determine the correction rather than the assumed 8.0% moisture content. Further, it has been determined that correcting the measurements that are taken at different moisture contents to standardized measurements based on about 7.5% moisture content provides a more accurate overall estimate of the standardized measurements compared to correcting the measurements to values that are based on standard ASTM laboratory conditions at the assumed 8.0% moisture content.

The correction is performed using a measurement of the moisture content of the sample during the time of measurement. In the preferred embodiment, the moisture of the small specimen fiber sample being tested is measured during the time of the measurement. Since the moisture content of the bulk fiber sample, of which small specimen fiber samples are taken, exhibits a distribution affecting the individual measurements, this will reduce the variations in the individual measurements of the different small specimen fiber samples. It has been found that the sample preparation process may significantly change the moisture content of the sample being measured. For this reason, it is preferred that the moisture measurement be of the moisture content of the sample during the time of measurement. This is preferably accomplished by measuring the moisture content of the small sample being measured or alternatively by proper design of the measuring instrument. The measurements are then adjusted using a correlation between the directly measured moisture content and the standard moisture content as described above in regard to testing in standard laboratory conditions. In this manner, measurements taken in nonstandard laboratory conditions can be compared to measurements taken in standard laboratory conditions.

The step of correcting the measurement is alternately accomplished by at least one of applying an algorithm that correlates measurements at different moisture contents, manipulating the measurement in a mathematical equation that correlates measurements at different moisture contents, and using a chart that correlates measurements at different moisture contents.

In some embodiments, the step of correcting the measurement includes correcting the measurement to a moisture content value other than about 7.5%, where the moisture content value is determined based at least in part on fiber characteristics such as at least one of geographical growth location including country and region, growth conditions including rainfall, sunlight, time of year, growth year, harvesting and ginning methods, fiber color, fiber type, and fiber trash content.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
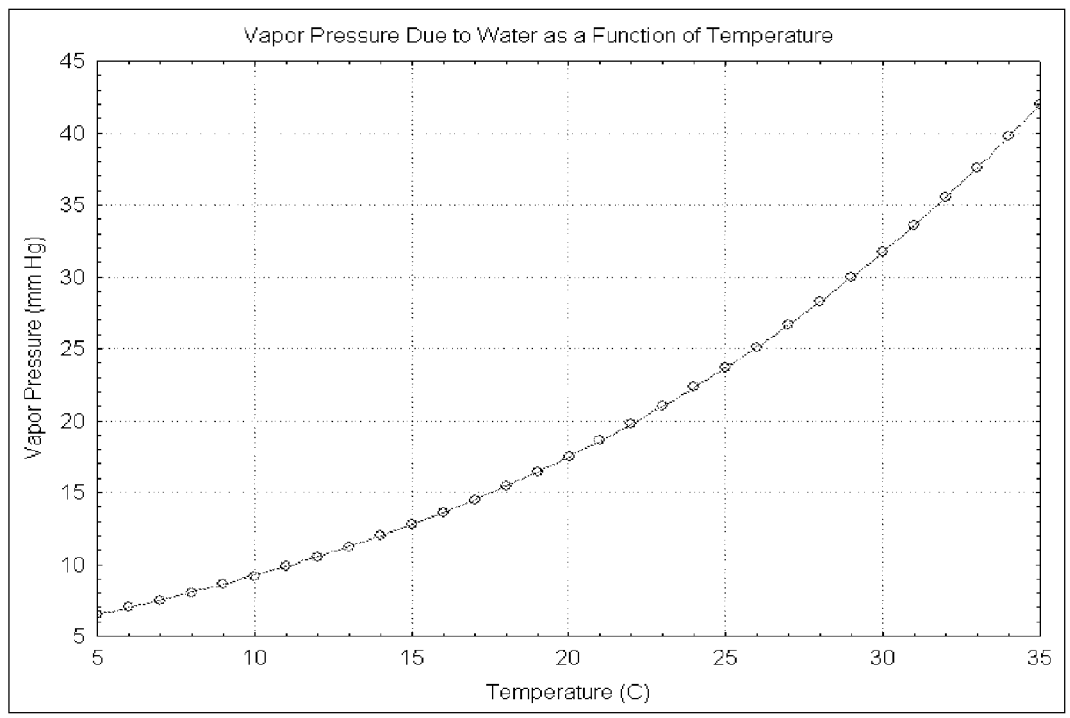
FIG. 1 depicts a graphical plotting of Maximum Moisture Content in Air versus Temperature.

Cotton samples gain or lose moisture in response to the moisture concentration in the ambient atmosphere. Relative humidity is defined as the percentage of moisture per liter of air compared to the maximum moisture per liter of air that will not produce condensation at that temperature. Relative humidity tends to be a relatively non-linear function within the range of interest as described herein. FIG. 1 depicts a graphical plotting of maximum moisture content in air versus temperature. As depicted, the relationship is not linear.

The actual moisture content in the air, such as measured in grams per liter, is determined by multiplying the relative humidity times the maximum value as determined by the temperature. Internationally used standards such as the American Society for Testing and Materials (ASTM) Standard Number D-1776 specify standard laboratory conditions at 21° Celsius +/−1° and 65% relative humidity +/−2%, in order to fix the amount of moisture content in the air during both conditioning and testing of the cotton fibers for characteristics such as length and strength. In order to allow the cotton sample time to acclimate to the laboratory conditions, the sample is required to remain in the laboratory for twenty-four hours before being tested.

Figure 2:
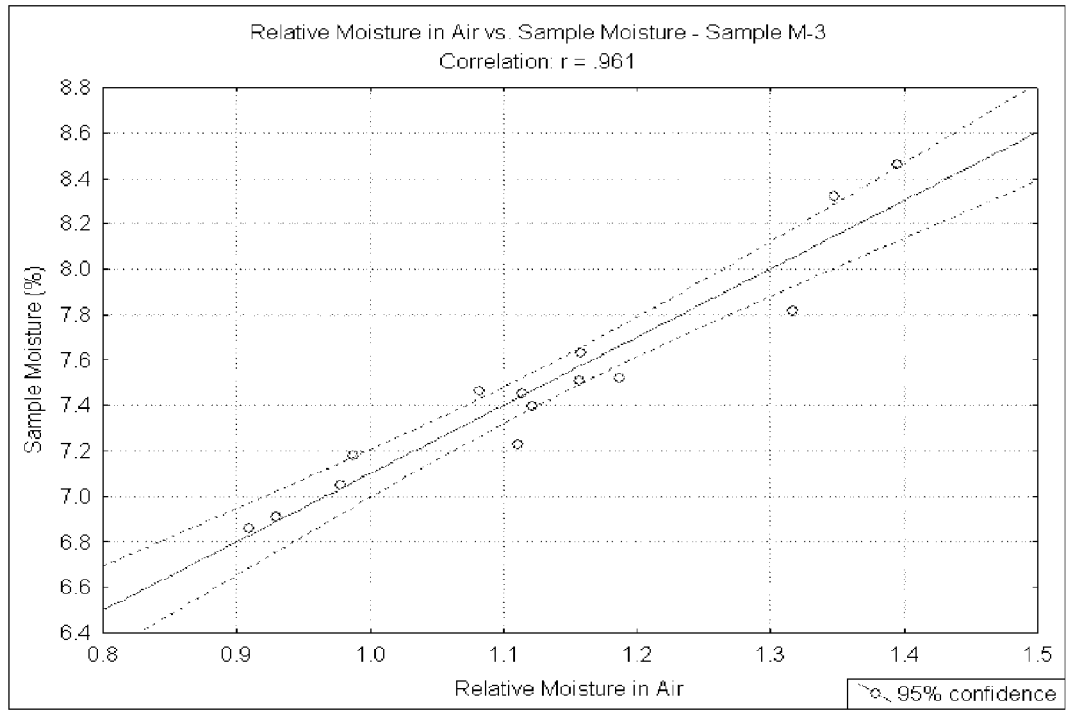
FIG. 2 depicts a graphical plotting of Measured Sample Moisture Content for Sample M-3 compared to relative moisture calculated from temperature and relative humidity.
Figure 3:
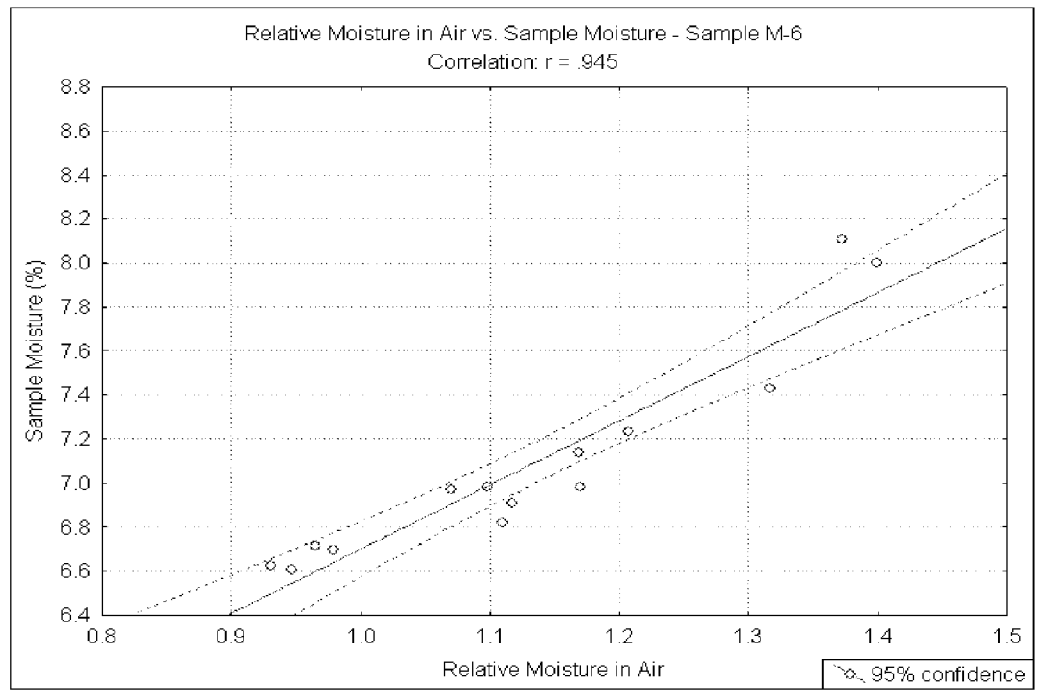
FIG. 3 depicts a graphical plotting of Measured Sample Moisture Content for Sample M-6 compared to relative moisture calculated from temperature and relative humidity.

In FIGS. 2 and 3, the cotton sample moisture content of the two different samples as actually and directly measured is compared to the relative moisture content in the air at different laboratory conditions. The relative moisture content is the ratio of the moisture content in the air at a given temperature and relative humidity as compared to that at standard laboratory conditions. As can be seen, the correlation between the relative moisture content and the actual sample moisture content as directly measured is fairly good for both samples but differs slightly between samples.

As mentioned above, the sample moisture content is important in fiber measurement because the physical properties of the fiber change due to the absorbed moisture. Without being bound by theory, it is believed that when the moisture penetrates the fiber, weak hydrogen bonds are formed between adjacent fiber sheaths. This results in increased fiber strength. The natural fiber crimp is also reduced, resulting in increased measured fiber length.

Figure 4:
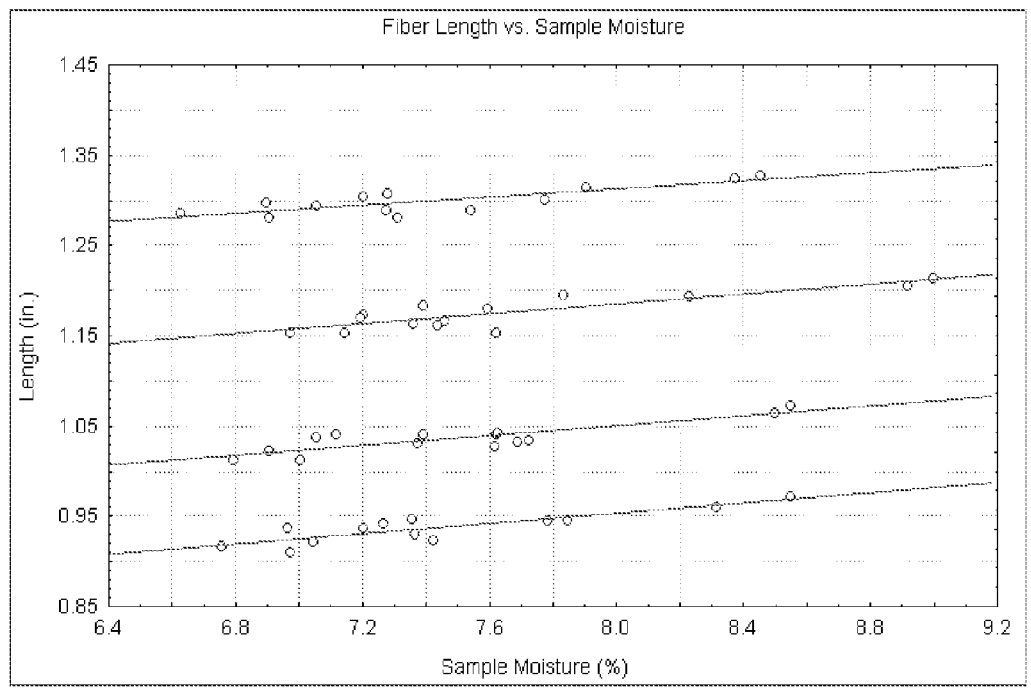
FIG. 4 depicts a graphical plotting of Measured fiber length as a function of sample moisture content for several different cotton samples.
Figure 5:
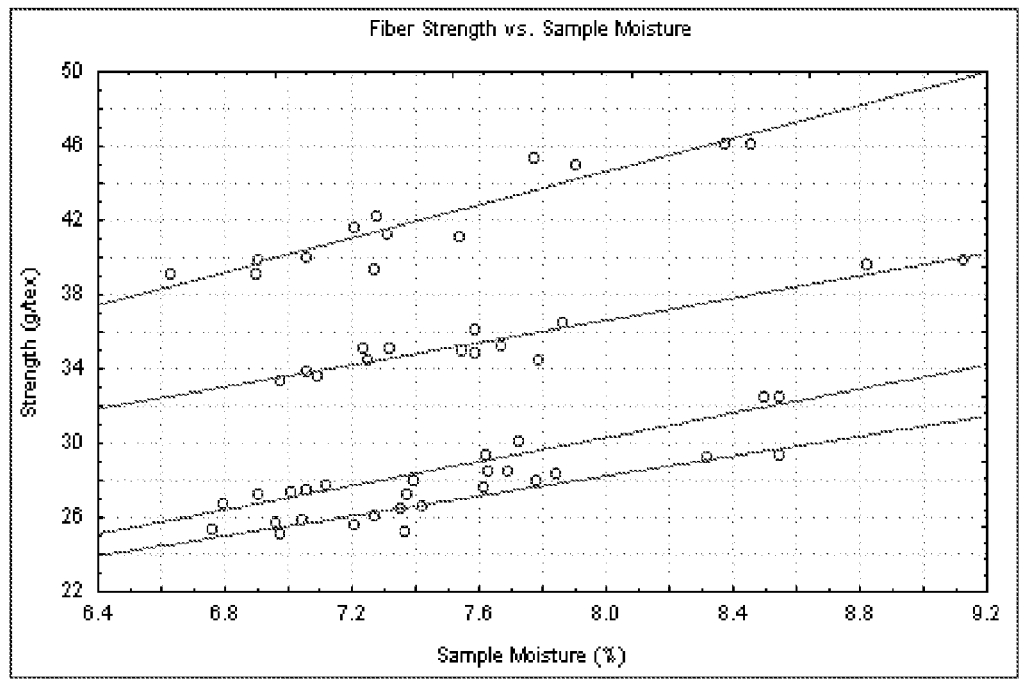
FIG. 5 depicts a graphical plotting of Measured fiber strength as a function of sample moisture content for several different cotton samples.

FIG. 4 depicts a graphical plotting of measured fiber length as a function of sample moisture content in four different cotton samples. As can be seen, the measured length of the fiber sample tends to increase as the moisture content increases. FIG. 5 depicts a graphical plotting of measured fiber strength as a function of sample moisture content in four different cotton samples. Again, as can be seen, the measured strength of the fiber sample tends to increase as the moisture content increases.

Figure 6:
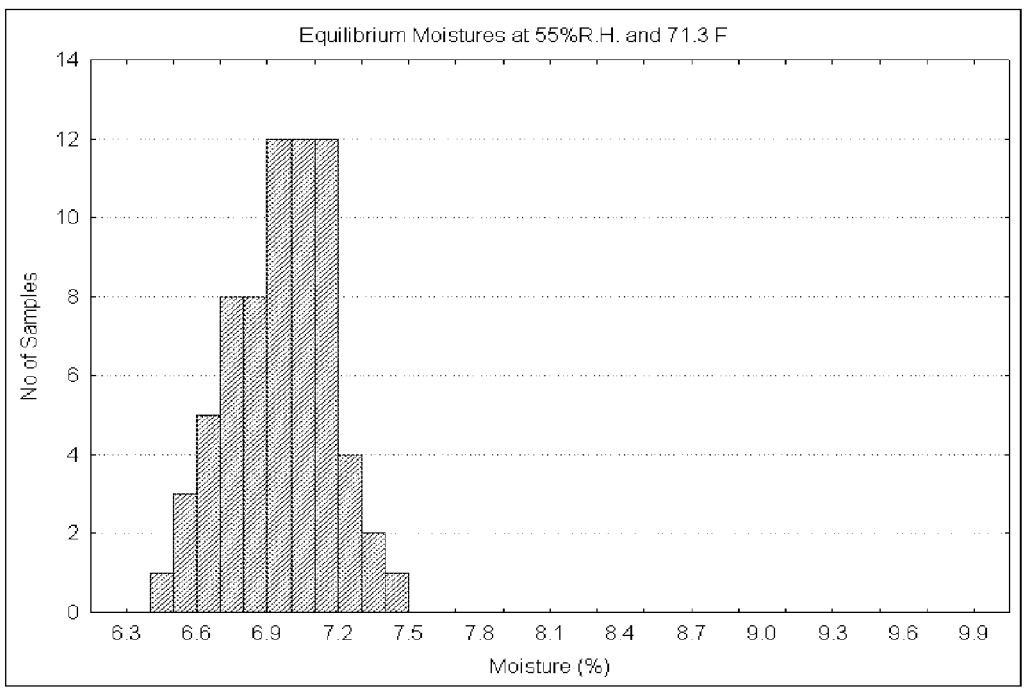
FIG. 6 depicts a graphical plotting of Measured fiber equilibrium moisture contents at 55% relative humidity and 71.3° Fahrenheit.
Figure 7:
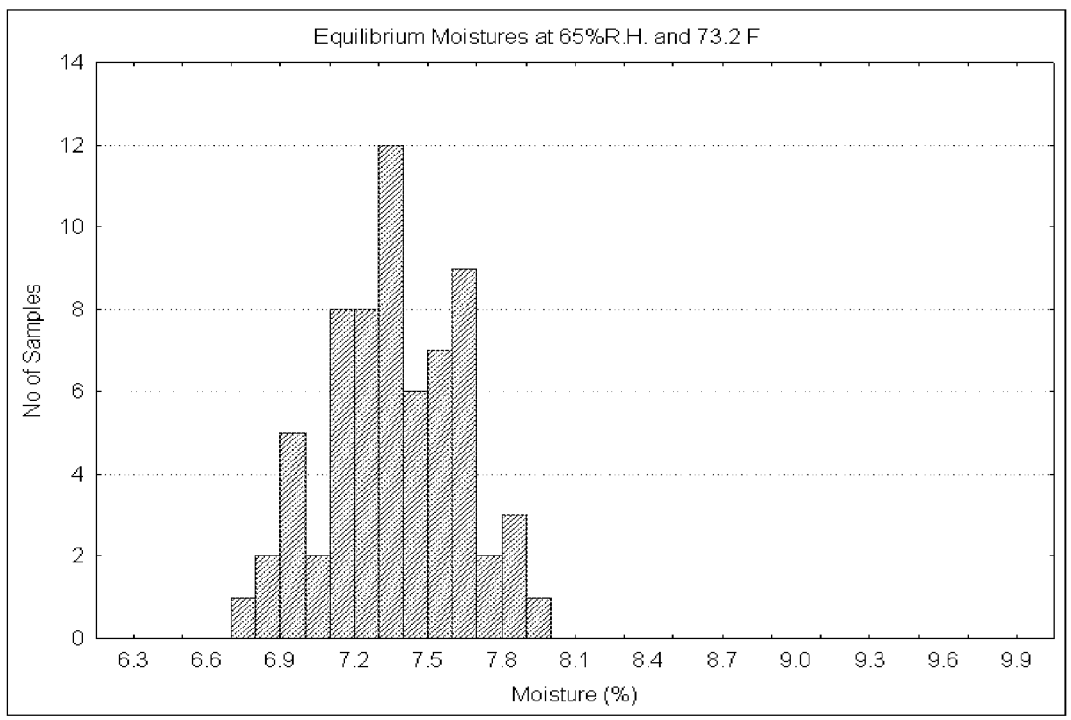
FIG. 7 depicts a graphical plotting of Measured fiber equilibrium moisture contents at 60% relative humidity and 71.8° Fahrenheit.
Figure 8:
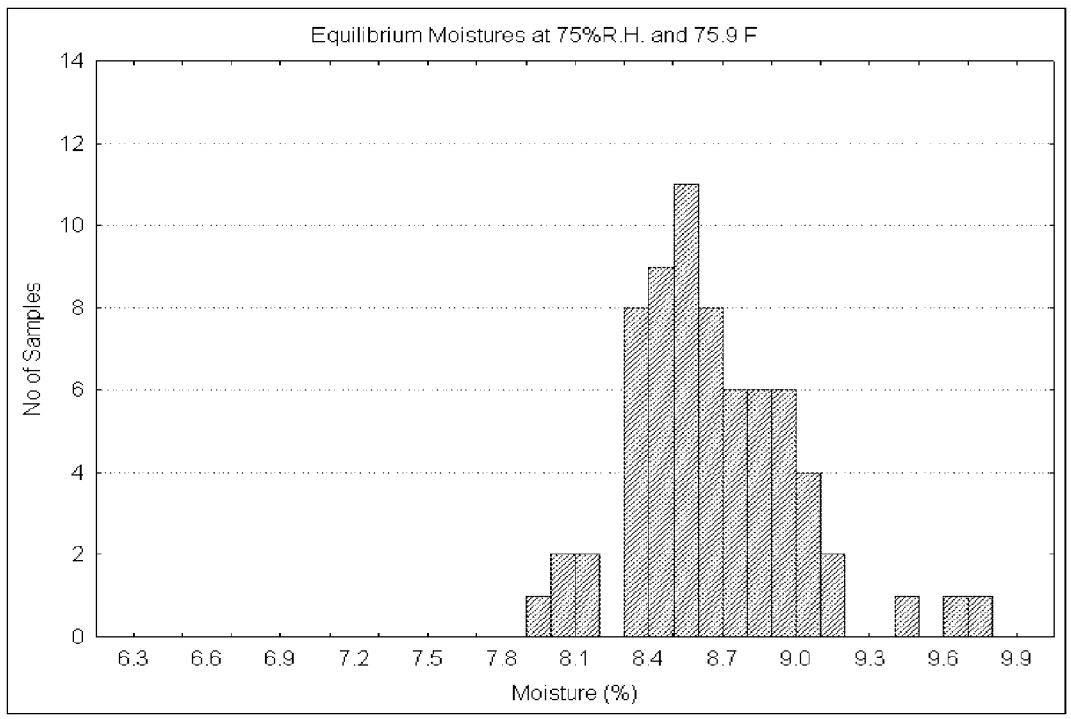
FIG. 8 depicts a graphical plotting of Measured fiber equilibrium moisture contents at 75% relative humidity and 75.9° Fahrenheit.

Based on these concepts, prior art methods previously corrected all measurements to measurements made at standard ASTM laboratory conditions with an assumed moisture content of 8.0%. However, different cotton samples equilibrate at different moisture contents under the same laboratory conditions. The histograms depicted in FIGS. 6-8 show the distributions of equilibrium moisture contents for different cotton samples under different laboratory conditions. As can be seen in each histogram, there is a spread in equilibrium moisture contents for each set of laboratory conditions, indicating that some samples had a relatively lower moisture content at the laboratory conditions stated, and some samples had a relatively higher moisture content at the laboratory conditions stated. Additionally, the moisture measurements were not representative of the sample moisture at the time of measurement due to either varying laboratory conditions or changes in the moisture of the sample being measured due to sample preparation processes.

Using data such as that described above, regression curves can be constructed for each cotton sample and the equilibrium moisture content can be calculated for any standard laboratory conditions. When this is done, the change in fiber measurements can be related to differences between the measured moisture content and the actual equilibrium moisture content for that sample rather than the assumed 8.0% moisture content. The importance of this discrepancy arises when attempting to calculate a group behavior for all samples. Unless a proper group behavior is analyzed, the resulting algorithm will not be robust, resulting in poor correlations between the corrected measurements and the actual measurements measured at standard ASTM laboratory conditions.

However, measurements can be made to correlate to measurements at any standard laboratory conditions with a greater degree of precision if additional characteristics of the cotton fiber sample are accounted for. As mentioned above, it has been determined that cotton samples tend to equilibrate to different moisture contents, even though they are held at the same laboratory conditions in terms of temperature and relative humidity. This indicates that the moisture content of a cotton fiber sample is dependent upon more variables than just temperature and relative humidity. It has been determined that the moisture content of a cotton fiber sample is additionally based on at least one of a variety of other fiber characteristics, including geographical growth location including country and region, growth conditions including rainfall, sunlight, time of year, growth year, harvesting and ginning methods, fiber color, fiber type, and fiber trash content.

This information can be used to more accurately standardize and correct the measurements made on fiber samples. For example, a fiber sample having known characteristics as mentioned above can be acclimated at the standard laboratory temperature and relative humidity. Then the moisture content for the fiber sample can be directly measured during the fiber measurements cycle. By directly measured it is meant that the moisture content is measured by a method or device that does not rely on a correlation to the temperature and relative humidity present in the laboratory. For example, such a method would include a resistance measurement. This process avoids errors due to sample moisture content distributions and changes in sample moisture content due to sample preparation processes.

Once the actual moisture content for the fiber sample is known, measurements taken at nonstandard laboratory conditions are then corrected to values that correlate to the actual moisture content as directly measured, rather than to some assumed moisture content value. By constructing charts in this manner of actual moisture contents based upon the varying characteristics as described above, a more accurate measurement data correction can be constructed. According to the more accurate measurement data correction, more than just the moisture content of the fiber sample is used to correct the measurements. Instead, the other characteristics as mentioned above are additionally used to determine the moisture content value to which the measurements should be corrected. In this manner, measurements taken on samples at standard laboratory conditions will compare more accurately with corrected measurements taken on samples at nonstandard laboratory conditions.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for standardizing at least one of a fiber strength reading and a fiber length reading taken on a fiber sample, the method comprising the steps of:

taking the reading on the fiber sample, measuring a moisture content of the fiber sample while taking the reading, where the moisture content is measured by a direct measurement on the fiber sample, correcting the reading to a standardized reading that adjusts for a difference between the measured moisture content of the fiber sample and a standardized moisture content.

2. The method of claim 1, wherein the step of correcting the reading is accomplished by an algorithm that correlates readings at different moisture contents.

3. The method of claim 1, wherein the step of correcting the reading is accomplished by using a chart that correlates readings at different moisture contents.

4. The method of claim 1, wherein the fiber sample is cotton.

5. The method of claim 1, wherein the step of correcting the reading comprises correcting the measurement to a moisture content other than about 7.5%, where the moisture content is determined based at least in part on fiber characteristics including at least one of country of growth, region of growth, rainfall during growth, sunlight during growth, time of year grown, growth year, harvesting method, ginning method, fiber color, fiber type, and fiber trash content.

* * * * *